United States Patent [19]

Nachbur et al.

[11] 3,931,310

[45] Jan. 6, 1976

[54] PHOSPHORUS-CONTAINING CONDENSATION PRODUCTS

[75] Inventors: Hermann Nachbur, Dornach; Arthur Maeder, Therwil, both of Switzerland

[73] Assignee: Ciba-Geigy AG, Basel, Switzerland

[22] Filed: Aug. 31, 1972

[21] Appl. No.: 285,268

[30] Foreign Application Priority Data

Sept. 10, 1971 Switzerland.................. 13304/71

[52] U.S. Cl............. 260/551 P; 252/8.1; 106/177; 117/136; 117/137; 260/2 P
[51] Int. Cl.[2]....................................... C07F 9/54
[58] Field of Search ................... 260/551, 2 P

[56] References Cited
UNITED STATES PATENTS 2,812,311  11/1957  Reeves et al............................ 260/2

FOREIGN PATENTS OR APPLICATIONS 740,269  11/1955  United Kingdom.................... 260/2

Primary Examiner—Harry I. Moatz
Attorney, Agent, or Firm—Joseph G. Kolodny; Prabodh I. Almaula; Edward McC. Roberts

[57] ABSTRACT

The subject of the invention is a process for the manufacture of water-soluble condensation products of hydroxymethyl-phosphonium compounds and dicyandiamide, characterised in that (a) 1 mol of a tetrakis-(hydroxymethyl)phosphonium compound is condensed with (b) 0.02 to 0.2 mol, preferably 0.05 to 0.15 mol, of an optionally methylolated dicyandiamide at 40° to 120°C, optionally in the presence of formaldehyde or a formaldehyde-donating agent, and an inert organic solvent, and optionally subsequently further condensed at temperature of 100° to 150°C, and if appropriate free hydroxyl groups are at least partially etherified with at least one alkanol with 1 to 4 carbon atoms and if appropriate the salts of the condensation products are converted into the corresponding hydroxides.

The condensation products are used for flameproofing organic fibre material, especially textiles.

9 Claims, No Drawings

PHOSPHORUS-CONTAINING CONDENSATION PRODUCTS

The subject of the invention is a process for the manufacture of water-soluble condensation products of hydroxymethyl-phosphonium compounds and dicyandiamide, characterised in that (a) 1 mol of a tetrakis-(hydroxymethyl)-phosphonium compound is condensed with (b) 0.02 to 0.2 mol, preferably 0.05 to 0.15 mol, of an optionally methylolated dicyandiamide at 40° to 120°C, optionally in the presence of formaldehyde or a formaldehyde-donating agent, and an inert organic solvent, and optionally subsequently further condensed at temperatures of 100° to 150°C, and if appropriate free hydroxyl groups are at least partially etherified with at least one alkanol with 1 to 4 carbon atoms and if appropriate the salts of the condensation products are converted into the corresponding hydroxides.

The condensation is preferably carried out at 70° to 110°C in an inert organic solvent or solvent mixture. For this, aromatic hydrocarbons are above all suitable, such as, for example, toluene, o-, m- or p-xylene or a mixture thereof, or xylene-toluene, xylene-benzene or xylene-decahydronaphthalene mixtures. Preferably, the further condensation which may follow is carried out at 125° to 140°C or especially about 135°C, that is to say the boiling point of the solvent or solvent mixture.

At the same time it is however also possible to carry out the condensation in the absence of an inert organic solvent, for example if condensation product already manufactured is used as the solvent or if condensation is carried out in the melt.

An appropriate procedure is to heat the tetrakis-(hydroxymethyl)-phosphonium compound, which as a rule is present as an aqueous solution, to the boil together with the component b), optionally in a solvent, and to distil off the water.

Possible tetrakis-(hydroxymethyl)-phosphonium compounds are above all salts and the hydroxide.

Suitable tetrakis-(hydroxymethyl)-phosphonium salts are, for example, the formate, acetate, phosphate or sulphate and the halides, such as, for example, the bromide or especially the chloride. Tetrakis-(hydroxymethyl)-phosphonium chloride is hereafter referred to as THPC.

Where tetrakis-(hydroxymethyl)-phosphonium hydroxide (THPOH) is used as the starting product, it is appropriately prepared beforehand from a corresponding salt, for example THPC, by neutralisation in aqueous solution with a base, for example sodium hydroxide, and subsequent dehydration.

Dicyandiamide can be used as such or in the methylolated form. Dicyandiamide itself is preferred. The formaldehyde which is optionally used conjointly is preferably present as an aqueous solution. The outstanding formaldehyde-donating agent is paraformaldehyde.

The etherification, which may have to be carried out, of the condensation product which still contains free hydroxyl groups is effected with, for example, n-butanol, n-propanol, ethanol or especially methanol. The reaction is preferably carried out in an acid medium.

The acid catalysts optionally used conjointly in the condensation are preferably salts which have an acid action (Lewis acids), such as magnesium chloride, iron-III chloride, zinc nitrate or boron trifluoride/diethyl ether. The conjoint use of these catalysts is especially advisable in the condensation of THPOH.

After completion of the condensation and optional etherification, the salts of the condensation products can also be completely or partially converted into their corresponding hydroxides, which is as a rule effected by adding strong bases such as alkali metal hydroxides or alkaline earth metal hydroxides, for example sodium hydroxide, potassium hydroxide or calcium hydroxide, or also sodium carbonate. The amount of base is appropriately so chosen that the pH value of the reaction mixture is about 5 to 8. Appropriately, this conversion is carried out in the bath used for application.

At times, the end products show an unpleasant odour caused by volatile, low molecular trivalent phosphorus compounds, for example phosphines, such as trihydroxymethylphosphine. This odour can be eliminated by an oxidative after-treatment of the condensation product, for example by passing air or oxygen into the reaction mixture or by adding oxidising agents such as hydrogen peroxide or potassium persulphate.

The condensation products are used for flameproofing organic fibre material, especially textiles. For this, an appropriate procedure is to apply to these materials an aqueous preparation which contains at least (1) a condensation product of the indicated type and (2) a polyfunctional compound which differs from the condensation products according to (1), and to finish the materials treated in this way by the thermofixing, moist batch, wet batch or ammonia fixing process. The thermofixing process is preferred.

The component (2) is preferably a polyfunctional epoxide or above all a polyfunctional nitrogen compound. Possible epoxides are above all epoxides which are liquid at room temperature and have at least two epoxide groups, which are preferably derived from polyhydric phenols. Polyfunctional nitrogen compounds are, for example, polyalkylenepolyamines or especially compounds which form aminoplasts, or aminoplast precondensates.

By compounds which form aminoplasts there are understood nitrogen compounds which can be methylolated and by aminoplast precondensates there are understood addition products of formaldehyde to nitrogen compounds which can be methylolated. As compounds which form aminoplasts or as nitrogen compounds which can be methylolated, there may be mentioned:

1,3,5-aminotriazines such as N-substituted melamines, for example N-butylmelamine, N-trihalogenomethylmelamines, triazones and ammeline, guanamines, for example benzoguanamines and acetoguanamines, or also diguanamines.

Further possibilities are: cyanamide, acrylamide, alkylurea or arylurea and alkylthioureas or arylthioureas, alkyleneureas or alkylenediureas, for example, urea, thiourea, urones, ethyleneurea, propyleneurea, acetylenediurea or especially 4,5-dihydroxyimidazolidine-2 and derivatives thereof, for example 4,5-dihydroxyimidazolidine-2 substituted in the 4-position, at the hydroxyl group, by the radical $-CH_2CH_2CO-NH-CH_2OH$. The methylol compounds of a urea, of an ethyleneurea or, especially, of melamine are preferentially used. Valuable products are in general given by products which are as highly methylolated as possible but in particular also by products with low methylolation such as etherified or non-etherified methylolmelamines, for example dimethylolmelamine or trimethylolmelamine or mixtures thereof. Suitable aminoplast precondensates are both predominantly monomolecular aminoplasts and also more highly precondensed aminoplasts.

The ethers of these aminoplast precondensates can also be used together with the reaction products. For example, the ethers of alkanols such as methanol, ethanol, n-propanol isopropanol, n-butanol or pentanols are advantageous. It is, however, desirable that these aminoplast precondensates should be water-soluble, such as, for example, pentamethylolmelaminedimethylether or trimethylolmelamine-dimethyl-ether.

The organic fibre materials which are to be provided with a flameproof finish are, for example, wood, paper, furs, hides or preferably textiles. In particular, fibre materials of polyamides, cellulose, cellulose-polyester or polyester are flameproofed, fabrics of wool or polyester or mixed fabrics of polyester and cellulose, wherein the ratio of the polyester constituent to the cellulose constituent is 1:4 to 2:1. It is thus possible to use, for example, so-called 20/80, 26/74, 50/50 or 67/33 polyester and cellulose mixed fabrics.

The cellulose or cellulose constituent of the fibre material originates, for example, from linen, cotton, rayon or staple viscose. In addition to polyester-cellulose fibre mixtures, fibre mixtures of cellulose with natural or synthetic polyamides can also be used. Above all, wool fibre materials can be flameproofed well with the condensation products.

The aqueous preparations for flameproofing the organic fibre materials as a rule contain 200 to 600 g/l, preferably 350 to 450 g/l, of the component (1) and 20 to 200 g/l, preferably 40 to 120 g/l, of the component (2). The preparations in most cases have an acid to neutral or weakly alkaline pH value.

The preparations for flameproofing can optionally contain yet further additives. To achieve a greater deposit of substance on fabrics it is advantageous, for example, to add 0.1 to 0.5%o of a high molecular polyethylene glycol. Furthermore, the customary plasticisers can be added to the preparations, for example an aqueous polyethylene emulsion.

To improve the mechanical strengths of the fibres it is also possible to add to the preparations suitable copolymers, for example copolymers of N-methylolacrylamide or cationic copolymers. Advantageous compositions for this purpose are, for example, aqueous emulsions of copolymers of (a) 0.25 to 10% of an alkaline earth metal salt of an $\alpha,\beta$-ethylenically unsaturated monocarboxylic acid, (b) 0.25 to 30% of a N-methylolamide or N-methylolamide-ether of an $\alpha,\beta$-ethylenically unsaturated monocarboxylic or dicarboxylic acid and (c) 99.5 to 60% of at least one other copolymerisable compound. These copolymers and their manufacture are known. The tear strength and abrasion resistance of the treated fibre material can be favourably influenced by the conjoint use of such a copolymer.

If a polymer of the indicated type is also added to the preparation, it is advantageously added in small amounts, for example 1 to 10% relative to the amount of the condensation product. The same is true of any plasticiser which may be added, where the appropriate amounts can again be 1 to 10%.

It is also possible to add curing catalysts, such as, for example, ammonium chloride, ammonium dihydrogen orthophosphate, phosphoric acid, magnesium chloride or zinc nitrate, but is in most cases not necessary.

The pH value of the preparations is as a rule 2 to 7.5, preferably 4 to 7, and is adjusted in the usual manner by adding bases or acids.

It can also be advantageous to add buffer substances, for example $NaHCO_3$, disodium and trisodium phosphate or triethanolamine.

To improve the durability of the flameproof finishes and to achieve a soft handle it can be advantageous to add, to the aqueous preparations, halogenated paraffins in combination with a polyvinyl halide compound or silicone oil emulsions.

The preparations are now applied to the fibre materials, which can be done in a manner which is in itself known. Preferably, piece goods are used, and are impregnated on a padder which is fed with the preparation at room temperature.

In the preferred thermofixing process, the fibre material impregnated in this way must now be dried and subjected to a heat treatment. Drying is appropriately carried out at temperatures of up to 100°C. Thereafter the material is subjected to a heat treatment at temperatures above 100°C, for example 100° to 200°C, preferably 120° to 180°C, the duration of which can be the shorter the higher is the temperature. This duration of heating is, for example, 30 seconds to 10 minutes.

It is, however, also possible to use the so-called moist fixing process or wet fixing process or the ammonia fixing process.

If the moist fixing process is used, the fabric is first dried to a residual moisture of about 5 to 20% and is thereafter stored for 12 to 48 hours at about 40° to 60°C, rinsed; washed and dried. In the wet fixing process a similar procedure is followed, except that the completely wet fibre material is stored. In the ammonia fixing process, the treated fibre material is gas-treated whilst still moist and is subsequently dried.

A rinse with an acid-binding agent, preferably with aqueous sodium carbonate solution, can be appropriate in the case of a strongly acid reaction medium.

In the examples which follow, the percentages and parts are percentages by weight and parts by weight, respectively. The relationship of parts by volume to parts by weight is as of ml to g.

EXAMPLE 1

244 parts of a 78% strength aqueous THPC solution (1 mol of THPC), 10.5 parts of dicyandiamide (0.125 mol) and 200 parts of xylene isomer mixture are heated to the boil, with rapid stirring, in a stirred vessel of 500 parts by volume capacity which is equipped with a water separator and thermometer. The azeotropic removal of the water from the aqueous THPC solution and of the water formed by condensation (a total of 79 parts of water) commences at a boiling point of 102°C. After removal of this amount of water, the boiling point rises up to 130°C without, however, further water being formed. The mixture is cooled to 90°C, the product is dissolved by adding 200 parts of water and the xylene is largely siphoned off. The aqueous solution is completely evaporated in vacuo at 70°C.

166 parts of a yellow, viscous condensation product, which forms a gel, but does not give a precipitate, with ammonia in aqueous solution, are obtained.

The infrared spectrum of the product shows the following bands:

| | | | |
|---|---|---|---|
| Broad | band at approx. | 3,240 cm⁻¹ | strong |
| Sharp | " | 2,910 " | weak |
| Broad shoulder | " | 2,850 " | medium |
| Broad shoulder | " | 2,640 " | medium |
| Broad shoulder | " | 2,350 " | weak |
| Sharp | " | 2,070 " | weak |
| Broad | " | 1,615 " | medium-strong |
| Broad | " | 1,410 " | medium |
| Sharp | " | 1,295 " | weak-medium |
| Broad shoulder | " | 1,200 " | weak-medium |
| Broad | " | 1,150 " | weak-medium |
| Sharp | " | 1,095 " | weak |
| Sharp | " | 1,040 " | medium |
| Sharp shoulder | " | 920 " | medium |
| Broad shoulder | " | 880 " | weak |

EXAMPLE 2

244 parts of a 78% strength aqueous solution of THPC (1 mol) and 10.5 parts of dicyandiamide (0.125 mol) are treated for 2 hours at 100° to 110°C internal temperature in a stirred vessel of 500 parts by volume capacity which is equipped with a thermometer and reflux condenser. Thereafter the water is removed in vacuo at 60°C.

190 parts of a yellowish, viscous condensation product which contains 15.5% of P and 3.4% of N are obtained.

The infrared spectrum of the product shows the following bands:

| | | | |
|---|---|---|---|
| Broad | band at approx. | 3,200 cm⁻¹ | strong |
| Sharp | " | 2,920 " | weak |
| Broad shoulder | " | 2,850 " | medium-strong |
| Broad shoulder | " | 2,620 " | medium |
| Broad shoulder | " | 2,350 " | weak |
| Sharp | " | 2,070 " | weak |
| Broad shoulder | " | 1,710 " | medium-strong |
| Broad | " | 1,630 " | medium |
| Broad | " | 1,530 " | weak |
| Broad | " | 1,410 " | medium |
| Sharp | " | 1,300 " | weak |
| Broad | " | 1,180 " | weak-medium |
| Broad | " | 1,160 " | weak-medium |
| Sharp | " | 1,040 " | strong |
| Broad | " | 920 " | medium-strong |
| Broad | " | 880 " | medium |

EXAMPLE 3

The procedure described in Example 1 is followed, but 12.6 parts of dicyandiamide (0.15 mol) are used.

160.5 parts of a yellowish, highly viscous condensation product are obtained and are diluted with water to 80% active substance content, in order to facilitate handling.

The infrared spectrum of the product shows the following bands:

| | | | |
|---|---|---|---|
| Broad | band at approx. | 3,200 cm⁻¹ | strong |
| Sharp | " | 2,920 " | weak |
| Broad shoulder | " | 2,850 " | medium |
| Broad shoulder | " | 2,640 " | medium |
| Broad shoulder | " | 2,480 " | weak-medium |
| Broad shoulder | " | 2,350 " | weak |
| Broad | " | 2,070 " | weak |
| Broad | " | 1,620 " | medium |
| Broad shoulder | " | 1,470 " | weak-medium |
| Broad | " | 1,410 " | medium |
| Sharp | " | 1,300 " | medium |
| Broad | " | 1,160 " | medium |
| Sharp | " | 1,040 " | strong |
| Sharp shoulder | " | 920 " | medium |
| Broad shoulder | " | 895 " | medium |

EXAMPLE 4

The procedure described in Example 1 is followed but 8.4 parts of dicyandiamide (0.1 mol) are used.

157 parts of a yellowish, highly viscous condensation product are obtained and are diluted with water to 80% active substance content in order to facilitate handling.

The infrared spectrum of the product shows the following bands:

| | | | |
|---|---|---|---|
| Broad | band at approx. | 3,200 cm⁻¹ | strong |
| Sharp | " | 2,920 " | weak |
| Broad shoulder | " | 2,850 " | medium |
| Broad shoulder | " | 2,640 " | medium |
| Broad shoulder | " | 2,350 " | weak |
| Broad | " | 2,080 " | weak |
| Broad | " | 1,630 " | medium |
| Broad | " | 1,415 " | medium |
| Sharp | " | 1,300 " | weak-medium |
| Broad | " | 1,165 " | medium |
| Sharp | " | 1,100 " | weak-medium |
| Sharp | " | 1,045 " | strong |
| Sharp shoulder | " | 920 " | medium |
| Broad shoulder | " | 900 " | medium |

EXAMPLE 5

244 parts of a 78% strength aqueous solution of THPC (1 mol) are neutralised to a pH value of 7.2 with 58 parts of 30% strength aqueous sodium hydroxide solution in a stirred vessel of 500 parts by volume capacity which is equipped with a thermometer and reflux condenser, and thereafter 10.5 parts (0.125 mol) of dicyandiamide are added. The mixture is then condensed for 2 hours at 100° to 110°C internal temperature. Thereafter the water is removed in vacuo at 60°C, the residue is dissolved in 80 parts of methanol and insoluble NaCl is separated off. After removing the methanol in vacuo at 50°C, 162 parts of a condensation product, which is a highly viscous paste, are obtained.

The infrared spectrum of the product shows the following bands:

| | | | |
|---|---|---|---|
| Broad | band at approx. | 3,200 cm⁻¹ | strong |
| Sharp | " | 2,910 " | weak |
| Broad shoulder | " | 2,850 " | medium |
| Broad shoulder | " | 2,640 " | medium |
| Sharp | " | 2,070 " | weak |
| Broad | " | 1,640 " | medium |
| Broad | " | 1,415 " | medium |
| Sharp | " | 1,295 " | weak |
| Broad | " | 1,145 " | weak |
| Sharp | " | 1,040 " | strong |
| Sharp shoulder | " | 920 " | medium |
| Broad shoulder | " | 880 " | medium |

EXAMPLE 6

488 parts of a 78% strength aqueous THPC solution (2 mols), 16.8 parts of dicyandiamide (0.4 mol) and 400 parts of xylene isomer mixture are heated to the boil, with rapid stirring, in a stirred vessel of 1,000 parts by volume capacity which is equipped with a water separator and thermometer. The azeotropic removal of the water from the aqueous THPC solution and of the water formed by condensation (a total of 162 parts of water) commences at a boiling point of 102°C. After removal of this amount of water, the boiling point reaches 132°C without, however, further water being formed. The mixture is cooled to 90°C, the product is dissolved by adding 400 parts of water and the xylene is largely siphoned off. The aqueous solution is completely evaporated in vacuo at 70°C.

330 parts of a yellow, viscous condensation product are obtained.

The infrared spectrum of this product shows the following bands:

| | | | |
|---|---|---|---|
| Broad | band at approx. | 3,200 cm$^{-1}$ | strong |
| Sharp | " | 2,920 " | weak |
| Broad shoulder | " | 2,850 " | weak-medium |
| Broad shoulder | " | 2,650 " | weak-medium |
| Broad shoulder | " | 2,480 " | weak |
| Broad shoulder | " | 2,360 " | weak |
| Sharp | " | 2,070 " | weak |
| Broad | " | 1,630 " | medium-strong |
| Broad | " | 1,410 " | weak-medium |
| Sharp | " | 1,295 " | weak |
| Broad shoulder | " | 1,205 " | weak |
| Broad | " | 1,150 " | weak |
| Broad | " | 1,090 " | weak |
| Sharp | " | 1,040 " | weak-medium |
| Broad | " | 895 " | weak-medium |

EXAMPLE 7

190.5 parts (1 mol) of crystalline anhydrous THPC and 1.7 parts (0.02 mol) of dicyandiamide are condensed for 2 hours in the melt, at 105°–110°C internal temperature, in a stirred vessel of 500 parts by volume capacity which is equipped with a reflux condenser and thermometer. After cooling, 190 parts of colourless waxy condensation product are obtained.

The infrared spectrum of this product shows the following bands:

| | | | |
|---|---|---|---|
| Broad | band at approx. | 3,240 cm$^{-1}$ | strong |
| Sharp | " | 2,920 " | weak |
| Broad shoulder | " | 2,850 " | medium |
| Broad shoulder | " | 2,630 " | medium |
| Sharp | " | 2,080 " | weak |
| Broad | " | 1,660 " | medium |
| Broad | " | 1,440 " | medium |
| Sharp | " | 1,300 " | weak |
| Sharp | " | 1,260 " | weak |
| Sharp | " | 1,040 " | strong |
| Sharp shoulder | " | 920 " | medium |
| Broad shoulder | " | 880 " | medium |

EXAMPLE 8

175 parts of the condensation product manufactured according to Example 7 are dissolved in 100 parts of methanol in the same apparatus, 0.1 part of 38% strength aqueous hydrochloric acid is added and the mixture is etherified for 30 minutes at the reflux temperature (64°–65°C). It is then cooled to 50°C and the excess methanol is removed in vacuo, whilst stirring, until constant weight is reached.

178 parts of a yellowish product, which partially crystallises, are obtained.

The infrared spectrum of this product shows the following bands:

| | | | |
|---|---|---|---|
| Broad | band at approx. | 3,240 cm$^{-1}$ | strong |
| Sharp | " | 2,910 " | weak |
| Broad shoulder | " | 2,820 " | medium |
| Broad shoulder | " | 2,610 " | medium |
| Broad shoulder | " | 2,360 " | weak-medium |
| Sharp | " | 2,070 " | medium |
| Broad | " | 1,630 " | medium-strong |
| Broad | " | 1,410 " | medium |
| Sharp | " | 1,295 " | weak |
| Broad | " | 1,195 " | weak |
| Broad | " | 1,040 " | medium-strong |
| Sharp shoulder | " | 920 " | medium |
| Broad shoulder | " | 880 " | weak-medium |

EXAMPLE 9

The procedure described in Example 2 is followed, but 11.4 parts (0.1 mol) of monomethyloldicyandiamide are used instead of the dicyandiamide.

194 parts of a crystalline white condensation product containing 15.9% of P are obtained.

The infrared spectrum of this product shows the following bands:

| | | | |
|---|---|---|---|
| Broad | band at approx. | 3,240 cm$^{-1}$ | strong |
| Sharp | " | 2,910 " | weak |
| Broad shoulder | " | 2,850 " | medium-strong |
| Broad | " | 2,610 " | medium |
| Broad shoulder | " | 2,470 " | weak |
| Broad shoulder | " | 2,350 " | weak |
| Sharp | " | 2,070 " | weak |
| Broad | " | 1,630 " | strong-medium |
| Broad | " | 1,410 " | medium |
| Sharp | " | 1,295 " | weak |
| Broad shoulder | " | 1,185 " | weak |
| Sharp shoulder | " | 1,160 " | weak |
| Sharp shoulder | " | 1,110 " | weak |
| Sharp | " | 1,040 " | strong |
| Sharp shoulder | " | 920 " | medium |
| Broad shoulder | " | 880 " | weak-medium |

EXAMPLE 10

244 parts (1 mol) of a 78% strength aqueous solution of THPC, 8.4 parts (0.1 mol) of dicyandiamide and 8.5 parts of formaldehyde (aqueous, 35.4% strength) are reacted with one another in accordance with Example 2.

194 parts of a viscous syrup are obtained.

The infrared spectrum of this product shows the following bands:

| | | | |
|---|---|---|---|
| Broad | band at approx. | 3,240 cm$^{-1}$ | strong |
| Sharp | " | 2,920 " | weak |
| Broad shoulder | " | 2,850 " | medium |
| Broad shoulder | " | 2,620 " | medium |
| Broad shoulder | " | 2,470 " | weak |
| Broad shoulder | " | 2,350 " | weak |
| Sharp | " | 2,070 " | weak-medium |
| Broad | " | 1,630 " | strong-medium |
| Broad | " | 1,410 " | medium |
| Sharp | " | 1,295 " | weak |
| Broad | " | 1,190 " | weak |
| Broad | " | 1,160 " | weak |
| Broad | " | 1,040 " | medium-strong |
| Sharp | " | 915 " | medium |
| Broad | " | 880 " | weak-medium |

EXAMPLE 11

Mixed fabrics of polyester/cotton (PES/CO), (67/33) or (50/50), are padded with the liquors according to Table 1 below, dried at 80 to 100°C and subsequently cured for 5 minutes at 150°C.

The fabric is then washed for 5 minutes at 60°C in a liquor which per litre contains 5 ml of hydrogen peroxide (35% strength), 3 g of aqueous sodium hydroxide solution (30% strength) and 1 g of a 25% strength aqueous solution of a condensation product of 1 mol of p-tert.-nonylphenol and 9 mols of ethylene oxide. Thereafter the fabric is rinsed and dried.

The degree of fixing indicates the amount of product present on the fibre after rinsing (relative to the amount originally taken up).

The fabrics are then washed up to 40 times for 45 minutes at 60°C in a domestic washing machine, using a liquor which contains 4 g/l of a domestic detergent (SNV 198,861 wash).

The individual fabric samples are then tested for their flameproof character (DIN 53,906 vertical test; ignition time 6 seconds).

The results are summarised in Table 1 below.

Table 1

| Constituents, g/l | Treated with liquor A | B | C | D |
|---|---|---|---|---|
| Product according to Example 1 | 550 | — | — | — |
| Product according to Example 2 | — | 550 | — | — |
| Product according to Example 3 | — | — | 485 | — |
| Product according to Example 4 | — | — | — | 485 |
| Dimethylolmelamine | 96.5 | 96.5 | 96.5 | 96.5 |
| pH value of the liquor (adjusted with NaOH) | 5.5 | 5.5 | 5.5 | 5.5 |
| Liquor uptake (%) | 75 | 75 | 75 | 75 |
| Degree of fixing (%), PES/CO 50/50 | — | 63 | — | — |
| PES/CO 67/33 | 78 | 67 | 75 | 76 |
| Flameproof character | PES/CO 67/33 | PES/CO 50/50 | PES/CO 67/33 | PES/CO 67/33 | PES/CO 67/33 |
| Tear length (cm) | | | | |
| After rinsing | 12.5 | 8.5 | 12 | 8.5 | 10 |
| After 20 washes (60°C) | 11 | 8 | 10 | 5.5 | 8 |
| After 40 washes (60°C) | 10.5 | 9 | — | 10 | — |

EXAMPLE 12

Fabrics of polyester/cotton (PES/CO), 67:33 and 50:50, wool (W) and cotton (CO) are padded with the liquors of Table 2 below, and then treated as follows:

a. By the thermofixing process, as indicated in Example 9, with subsequent washing at 60°C as indicated in Example 9.

b. Partly by the moist fixing or moist batch process: After padding store at 10% residual moisture content for 24 hours at 50°C, subsequently rinse with cold water, wash for 5 minutes in a bath which contains 4 g/l of calcium carbonate and 1 g/l of a condensation product of 1 mol of p-tert.nonylphenol and 4 mols of ethylene oxide, then rinse and dry.

c. Partly by the wet fixing or wet batch process: After padding store wet for 24 hours at 50°C and subsequently rinse and wash as under b).

The fabrics are then washed up to 20 times, as indicated in Example 11, at 40° (W), 60°C (PES/CO) and at the boil (CO), and thereafter tested for their flameproof character according to DIN 53,906 (ignition time 6 seconds). Untreated fabrics burn away.

The results are summarised in Table 2 below.

Table 2

| Constituents of the liquor, g/l Fabric | CO | PES/CO 67/33 | PES/CO 50:50 | | Wool | | |
|---|---|---|---|---|---|---|---|
| Fixing process | a) | a) | a) | b) | a) | b) | c) |
| No. | I | II | II | III | IV | IV | IV |
| Product according to Example 5 | 183 | 425 | 425 | 425 | 350 | 350 | 350 |
| Di-Trimethylolmelamine | 96.5 | 103 | 103 | 103 | 84.5 | 84.5 | 84.5 |
| Product [+) ] | — | — | — | 2 | 2 | 2 | 2 |
| Silicone oil emulsion (40% strength) | 35 | 35 | 35 | 35 | 35 | 35 | 35 |
| pH value of the liquor | 5.5 | 5.5 | 5.5 | 4.5 | 5.5 | 4.5 | 4.5 |
| Liquor uptake, % | 80 | 70 | 70 | 70 | 80 | 80 | 80 |
| g of phosphorus/kg of fabric | 28 | 57 | 57 | 57 | 54 | 54 | 54 |
| g of nitrogen/kg of fabric | 32 | 30 | 30 | 30 | 28 | 28 | 28 |
| Flameproof character: Burning time (seconds) / Tear length (cm) | | | | | | | |
| After rinsing | 0/10 | 0/7 | 0/7.5 | 0/8 | 0/7 | 0/9 | 0/5 |
| After 1 wash | 0/8 | 0/7 | 0/6 | 0/7.5 | 0/4 | 0/6 | 0/3 |
| After 5 washes | 0/7.5 | 0/8.5 | 0.8 | 0/7.5 | 0/7 | 0/4 | 0/3 |
| After 20 washes | 0/8 | 0/10 | 0/7 | 0/10 | 0/6 | 0/8.5 | 0/6 |

+) Condensation product of 1 mol of p-nonylphenol and 9 mols of ethylene oxide.

EXAMPLE 13

A polyester fabric is padded with an aqueous liquor which contains 420 g/of the product according to Example 5, 120 g/l of di-trimethylolmelamine and 35 g/l of a silicone oil emulsion (40% strength) and has a pH value of 5.5 or 4.5. The liquor uptake is 80%. The amounts used are so chosen that the liquors contain 64 g of phosphorus and 32 g of nitrogen per kg of fabric.

The impregnations are fixed according to methods (a) and (b) of Example 12, rinsed and subjected to one wash according to SNV 198,861, as described in Example 11.

Thereafter the test specimens are tested for their flameproof character according to DIN 53,906. Untreated fabrics burn away.

The results are summarised in Table 3 below.

Table 3

| | Flameproof character: Burning time (seconds) / tear length (cm) | |
|---|---|---|
| | Thermofixing process | Moist fixing process |
| After rinsing | 4 / 14 | 4 / 14 |

Table 3-continued

| Flameproof character: Burning time (seconds) / tear length (cm) | | |
|---|---|---|
| | Thermofixing process | Moist fixing process |
| After 1 wash | 6 / 12 | 13 / 14 |

EXAMPLE 14

Mixed fabrics of polyester-cotton (PES/CO), 50:50 and 67:33, are padded with the liquors according to Table 4 below, dried for 30 minutes at up to about 80°C and subsequently cured for 5 minutes at 150°C. The phosphorus content and the nitrogen content are 57 g and 30 g respectively, per kg of fabric.

The fabric is then washed for 5 minutes at 60°C in a liquor, rinsed and dried as indicated in Example 11.

The fabrics are then washed up to 20 times for 45 minutes at 60°C in a domestic washing machine, as indicated in Example 11.

The individual fabric samples are then tested for their flameproof character (DIN 53,906 vertical test; ignition time 6 seconds).

The results are summarised in Table 4 below.

Table 4

| | Fabric treated with liquor | | | | | | | |
|---|---|---|---|---|---|---|---|---|
| Constituents, g/l | PES/CO 67/33 | | | | PES/CO 50/50 | | | |
| | I | II | III | IV | I | II | III | IV |
| Product according to: | | | | | | | | |
| Example 6 | 450 | | | | 450 | | | |
| Example 8 | | 510 | | | | 510 | | |
| Example 9 | | | 510 | | | | 510 | |
| Example 10 | | | | 510 | | | | 510 |
| Di-Trimethylolmelamine | 103 | | 103 | 103 | 103 | | 103 | 103 |
| Trimethylolmelamine-dimethyl-ether (75% strength) | | 153 | | | | 153 | | |
| Silicone oil emulsion (40% strength) | 35 | 35 | 35 | 35 | 35 | 35 | 35 | 35 |
| pH value of the liquor | 7 + | 5.5 | 4.5 | 5.5 | 7 + | 5.5 | 4.5 | 5.5 |
| Degree of fixing, % | 79 | 57 | 65 | 63 | 66 | 58 | 68 | 61 |
| Flameproof character: Burning time (seconds) / Tear length (cm) | | | | | | | | |
| After rinsing | 0/8.5 | 0/11 | 0/7.5 | 0/11 | 0/8 | 0/7 | 0/7 | 0/9 |
| After 1 wash | 0/7 | 0/8 | 0/10 | 0/7.5 | 0/5 | 0/6 | 0/5 | 0/6.5 |
| After 5 washes | 0/6.5 | 0/10 | 0/5 | 0/6.5 | 0/5 | 0/13 | 0/5 | 0/8 |
| After 20 washes | 0/8 | 0/11 | 0/10 | 0/10 | 0/6 | 0/9 | 0/10 | 0/10 |

+The salts of the condensation products have been converted into their corresponding hydroxides by adjusting the pH value of the liquor to 7 by means of sodium hydroxide.

EXAMPLE 15

Mixed fabrics of polyester-cotton PES/CO (50/50 and 67/33) are padded with the liquor according to Table 5 below and finished according to the ammonia fixing process.

In this process, the padded fabric is dried incompletely (about 10 to 20% residual moisture content) at up to 80°C and is then gassed for 10 minutes with ammonia. Thereafter it is treated with a liquor which contains 300 ml of a 24% strength aqueous ammonia solution per litre, using a liquor ratio of 1:30. It is then washed, unrinsed, at 40°C in a bath which contains 5 g/l of soap and 6 ml/l of $H_2O_2$ (35% strength), and then rinsed and dried.

The fabrics are then washed up to 20 times for 45 minutes at 60°C in a domestic washing machine, in a liquor which contains 4 g/l of a domestic detergent (SNV 198,861 wash). The individual fabric samples are then tested for their flameproof character (DIN 53,906 vertical test; ignition time 6 seconds).

The results are summarised in Table 5 below.

Table 5

| Constituents | Liquor |
|---|---|
| Product according to Example 9 | 515 |
| Di-Trimethylolmelamine | 103 |
| Silicone oil emulsion | 35 |
| pH value | 4.5 |
| g of phosphorus/kg of fabric | 57 |
| g of nitrogen/kg of fabric | 30 |

| Test of flameproof character: | Burning time (seconds) / Tear length (cm) | |
|---|---|---|
| | PES/CO 50:50 | PES/CO 67:33 |
| After rinsing | 0/9.5 | 0/9.5 |
| After 1 wash | 0/8.5 | 0/10.5 |
| After 5 washes | 0/8.5 | 0/11 |
| After 20 washes | 0/8.5 | 0/11 |
| Untreated fabric burns away. | | |

We claim:

1. A water-soluble condensation product from tetrakis-(hydroxymethyl)-phosphonium compound and dicyandiamide, produced by the process, comprising condensing a tetrakis-(hydroxymethyl)-phosphonium salt or tetrakis(hydroxymethyl)-phosphonium hydroxide with dicyandiamide or methylolated dicyandiamide, at a molar ratio of 1:0.02 to 0.2, at 40° to 120°C in the presence of an inert organic solvent or aqueous medium or in the melt, to give the condensation product, while simultaneously removing by distillation from the reaction mixture any water present or formed during the condensation.

2. A product of claim 1, wherein further condensation occurs as the reaction temperature is elevated to 100° to 150°C after removal of the water.

3. A product of claim 1, wherein the resulting product is further treated with an alkanol of 1 to 4 carbon atoms in an acid medium to effect partial or complete etherification.

4. A product of claim 1, wherein reaction mixture further includes formaldehyde or paraformaldehyde.

5. A product of claim 1, wherein the tetrakis-(hydroxymethyl)-phosphonium compound is treated with dicyandiamide.

6. A product of claim 1, wherein the inert organic solvent is an aromatic hydrocarbon solvent.

7. A product of claim 1, wherein the molar ratio is 1:0.05 to 0.15.

8. A product of claim 1, wherein the tetrakis-(hydroxymethyl)-phosphonium salt is a tetrakis(hydroxymethyl)-phosphonium halide.

9. A product of claim 8, wherein the tetrakis-(hydroxymethyl)-phosphonium halide is tetrakis(hydroxymethyl)-phosphonium chloride.

* * * * *